US005527803A

United States Patent [19]
Halazy et al.

[11] Patent Number: 5,527,803
[45] Date of Patent: Jun. 18, 1996

[54] 9-PURINYL PHOSPHONIC ACID DERIVATIVES

[75] Inventors: Serge Halazy, Wolfisheim; Charles Danzin, Strasbourg, both of France

[73] Assignee: Merrell Pharmaceuticals Inc., Cincinnati, Ohio

[21] Appl. No.: 469,097

[22] Filed: Jun. 6, 1995

Related U.S. Application Data

[62] Division of Ser. No. 336,703, Nov. 8, 1994, which is a continuation of Ser. No. 721,791, Jun. 26, 1991, abandoned.

[30] Foreign Application Priority Data

Jul. 4, 1990 [EP] European Pat. Off. ............. 90401940

[51] Int. Cl.$^6$ .................................................... A61K 31/52
[52] U.S. Cl. ................ 514/263; 514/81; 514/261; 514/262; 514/885; 544/264; 544/265; 544/266; 544/267
[58] Field of Search ............................. 536/26.7, 26.71; 544/264, 265, 266, 267; 514/45, 47, 48, 261, 262, 81, 263, 885

[56] References Cited

U.S. PATENT DOCUMENTS

| | | | |
|---|---|---|---|
| 4,927,830 | 5/1990 | Townsend et al. | 514/258 |
| 4,988,680 | 2/1991 | Halazy et al. | 514/81 |
| 4,988,702 | 1/1991 | Kostlan et al. | 514/258 |

FOREIGN PATENT DOCUMENTS

| | | |
|---|---|---|
| 173624 | 3/1986 | European Pat. Off. . |
| 0328834 | 2/1988 | European Pat. Off. . |
| 0331550 | 2/1989 | European Pat. Off. . |
| 0335770 | 3/1989 | European Pat. Off. . |
| 338887 | 10/1989 | European Pat. Off. . |
| 338168 | 10/1989 | European Pat. Off. . |
| 374096 | 6/1990 | European Pat. Off. . |
| 375164 | 6/1990 | European Pat. Off. . |
| 0468119 | 7/1990 | European Pat. Off. . |
| 0477454 | 9/1990 | European Pat. Off. . |
| 0465297 | 6/1991 | European Pat. Off. . |
| 0468866 | 7/1991 | European Pat. Off. . |
| 0479640 | 9/1991 | European Pat. Off. . |
| 2124898 | 5/1990 | Japan . |
| 2124897 | 5/1990 | Japan . |
| 8404748 | 12/1984 | WIPO . |

OTHER PUBLICATIONS

Halazy et al., Bioorganic & Medicinal Chemistry Letters, vol. 2, No. 5, pp. 407–410, (1992).
Kelley et al., J. Med. Chem., vol. 36, No. 22, pp. 3455–3463, (1993).
Erion et al., J. Med. Chem., vol. 37, p. 1034, (1994).
Weibel et al., Biochemical Pharmacology, vol. 48, No. 2, pp. 245–252, (1994).
Chemical Abstracts, vol. 106, p. 771, 1987, 106:176792f, abstracting Davisson, V. J., et al., relates to the "Synthesis of nucleotide 5'-diphosphates from 5'-O-tosyl nucleosides," J. Org. Chem. 52(9), 1794–801, 1987.
Nakamura, C. E., et al, Biochemical Pharmacology, vol. 35, No. 2, pp. 133–136, 1986.
Stoeckler, J. D., et al., Federation Proceedings, vol. 25, No. 12, pp. 2773–2778, 1986.
Daddona, P. E., et al., The Journal of Biological Chemistry, vol. 261, No. 25, pp. 11667–11673, 1986.
Suzuki, et al., Biochemical and Biophysical Research Communications, vol. 156(3):1144–1151 (Nov. 16, 1988).
Back, et al., Br. J. Clin. Pharmac. 33:319–322 (1992).
Stoeckler, J. D., et al., Biochemistry 19, 102–107 (1980).
Cooney, D. A., et al., Biochemical Pharmacology 36(11), 1765–1768 (1987).
Pauwels, R., et al., Bioch. Pharm. 37(7), 1317–1325 (1988).
Baba, M., et al., Biochem. Biophys. Res. Comm. 145(3), 1080–1086 (1987).
Sanghvi, Y. S., et al., J. Med. Chem 21, 330–335 (1988).
Ahluwalia, G., et al., Biochem. Pharmacology 36(22), 3797–3800 (1987).
Stein, J. M., et al., Biochemical Pharmacology, vol. 36, No. 8, pp. 1237–1244, 1987.
Prisbe, E. J., et al., J. Med. Chem. 29, 671–675, 1986.

*Primary Examiner*—Douglas W. Robinson
*Assistant Examiner*—James O. Wilson
*Attorney, Agent, or Firm*—William R. Boudreaux

[57] ABSTRACT

This invention relates to novel purine nucleoside phosphorylase inhibitors, to the methods and intermediates for their preparation and to their use as immuno-suppressants, antilymphoma, antileukemic, antiviral and antiprotozoal agents.

4 Claims, No Drawings

9-PURINYL PHOSPHONIC ACID DERIVATIVES

CROSS-REFERENCE TO RELATED APPLICATIONS

This is a division of application Ser. No. 08/336,703, filed Nov. 8, 1994, which is a continuation of application Ser. No. 07/721,791 filed Jun. 26, 1991, now abandoned which is herein incorporated by reference.

FIELD OF THE INVENTION

This invention relates to novel purine nucleoside phosphorylas inhibitors, to the methods and intermediates for their preparation and to their use as immuno-suppressants, antilymphoma, antileukemic, antiviral and antiprotozoal agents.

BACKGROUND

Purine nucleoside phosphorylase (PNP) under normal in vivo conditions catalyzes the phosphorolytic cleavage of the ribo- and deoxyribonucleosides of guanine and hypoxanthine to the corresponding sugar phosphate and guanine or hypoxanthine. In the absence of PNP, uric acid concentration is quite low while the concentration of certain nucleoside substrates of PNP such as (dGuo) in plasma and urine are elevated. dGuo is toxic towards lymphoblasts, however, T-cells are much more affected than are B-cells. Indeed, in patients with genetically acquired PNP deficiency, B-cell immunoglobulin production is normal or even elevated, but these patients are leukopenic and T-lymphocytic function is either totally lacking or is severely depressed. While uncontrolled PNP deficiency is obviously undesirable, there are many instances where controlled suppression of the immune system, and in particular controlled supression of T-cells, would be highly desirable such as in the treatment of T-cell leukemia, the suppresion of host-vs-graft response in organ transplant recipients, and the treatment of gout. Applicants have discovered a class of 9-purinyl phosphonic acid derivatives which are potent inhibitors of PNP and are thus useful as immunosuppressant agents.

SUMMARY OF THE INVENTION

More specifically this invention relates to novel purinyl phosphonic acid derivatives of the formula

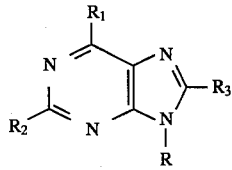

the tautomeric forms thereof, and the pharmaceutically acceptable salts thereof, wherein

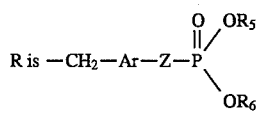

with Ar being a bridging moiety to which its adjacent $CH_2$ moiety is bonded to one ring carbon atom and the Z moiety is bonded to a second ring carbon atom of an $R_9$-substituted phenyl, thiophene or furan moiety, Z is a moiety of sub-types (a), (b), (c), (d), or (e) wherein (a) is

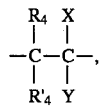

(b) is

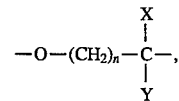

(c) is

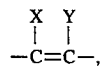

(d) is —C≡C—, _nd
(e) is

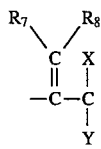

with the proviso that when Z is a sub-type (b) moiety, then Ar is other than a furan or thiophene moiety, n is an integer of 1 to 5 or zero, $R_1$ is —OH or —SH,
$R_2$ is H or —$NH_2$,
$R_3$ is H, —$NH_2$, —OH or —NH—$NH_2$,
$R_4$ is H,
$R'_4$ is H OH or F or $R_4$ and $R'_4$, together with the carbon atom to which they are attached, form a keto moiety,
$R_5$ is $C_{1-6}$ alkyl or $R'_5$,
$R_6$ is $C_{1-6}$ alkyl or $R'_6$ with $R'_5$ and $R'_6$ being H each of
$R_7$ and $R_8$ is H, F, or $C_{1-4}$ alkyl,
$R_9$ is H, Cl, Br, $C_{1-6}$ alkyl, $C_{1-6}$ alkoxy, OH, $NH_2$ or $CH_3$ with the proviso that when Ar is furan or thiophene, $R_9$ is other than OH or $NH_2$,
X and Y are H, F or Cl, with the proviso that when n is zero X and Y are both H.

As used herein the terms $C_{1-4}$ or $C_{1-6}$ alkyl include the straight and branched saturated lower aliphatic hydrocarbyl moieties having up to 4 or 6, respectively, carbon atoms including methyl, ethyl, propyl, isopropyl, sec-butyl, n-butyl, t-butyl, pentyl and the like; the $C_{1-6}$ alkoxy moieties being ether derivatives thereof. The "Ar" moiety bridging its contiguous $CH_2$ and Z moieties are $R_9$-substituted phenyl, furan or thiophene moieties wherein phenyl may be bridged at its 1,2-, 1,3- or 1,4-positions, and each of furan and thiophene may be bridged through the 2,3-, 2,4-, 2,5, or 3,4-position ring carbon atoms; the $R_9$-substitution may be mono- or di-substituted, substitution being at any of the other available ring carbon atoms. Tautomeric enol-keto forms may exist at the 6-position of the purine nucleus.

The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate.

Illustrative organic acids which form suitable salts include the mono-, di-, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. Either the mono- or the di-acid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased stability.

The preparation of the compounds of formula I may, in general, be effected by a condensation reaction wherein a 6-chloro purine (2) is treated with an activated (—$CH_2$—Ar—Z—)-substituted phosphonate (3) and the resulting Ia intermediate converted to the appropriate R, $R_1$, $R_2$, $R_3$-substituted purine derivatives of formula I. The general condensation reaction is depicted in the following reaction scheme.

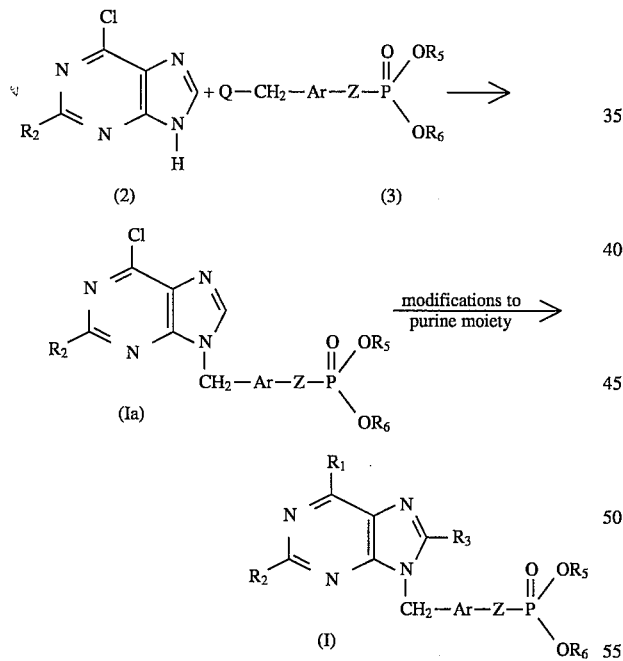

wherein $R_1$, $R_2$, $R_3$, Ar, Z, $R_5$ and $R_6$ are as previously defined, except that $R'_4$ which occurs when Z is a moiety of sub-type (a) may also be a silyl ether, and Q is bromo, iodo or hydroxy.

In those instances wherein it is desired to effect a condensation of the 6-chloro purine intermediate (2) with a phosphonoaryl (3) wherein Q is a halide, the condensation is effected by reacting a slight excess (about 10%) of the 6-Cl purine reactant (2) in the presence of a base such as sodium hydride (NaH), potassium carbonate ($K_2CO_3$) or cesium fluoride (CsF) (in amounts of about 2 equivalents) in a non-reactive solvent such as dimethylformamide (DMF) within a temperature range of about 0° to 60° C., preferably at room temperature for about 4 to 18 hours.

In the instance wherein Q is OH, the condensation is effected under more neutral conditions according to the Mitsunobu-type reaction using diethyl azodicarboxylate (DEAD) in the presence of P(R')$_3$ wherein R' is preferably phenyl but including methyl and isopropyl, said reaction being conducted in a suitable non-reactive solvent at 0° to 60° C.

Of course in each instance, in those reactions wherein the Ar moiety bears an $R_9$-substitutent which may be affected by the reaction conditions of these condensations (or modifications of the purine base) then such substituents are modified to obviate any undesired side-reactions and, at the appropriate step, are reconverted back to the desired form. For example, if $R_9$ is OH, then an intermediate ester or ether derivative can be formed, and at the appropriate step, the ester or ether may be hydrolyzed back to its alcohol. These principles are well-understood by those of ordinary skill in the art and need not be detailed herein.

In the special instance wherein $R_4$, $R'_4$, X and Y of formula (3) are all hydrogen, it is preferred to condense a bromomethyl derivative of the phosphonylaryl of the formula

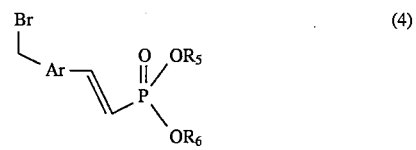

with the purine (2) and hydrogenate the resulting products preferably using hydrogen gas in the presence of palladium on carbon ($H_2$-Pd/C) according to standard techniques.

In the special instance wherein it is desired to prepare compounds of formula Ia wherein $R_4$ is H and $R'_4$ is OH or $R_4$ and $R'_4$ form a keto moiety (as defined above) it is prepared to use a silyl ether, (preferably t-butyl dimethylsilyl ether), to protect the hydroxy moiety of the phosphonyl halide, i.e.,

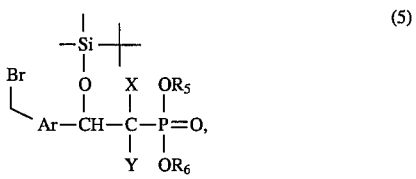

wherein

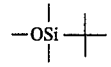

represents a t-butyl dimethylsilyl ether and following the condensation, as previously described, remove the silyl protecting group by acid hydrolysis. If the resulting alcohol is to be oxidized, the alcohol can be oxidized to the desired ketone by use of the Swern oxidation reaction. In practice it is preferred to form the silyl ether prior to activating the reactants of formula 3, as herein below described.

The "Q-activated" reactants of formula 3 may be prepared by methods well known in the art, preferably utilizing intermediates wherein the OH groups (if any) are reaction-protected prior to activation with either the halo or hydroxy moieties.

Preferably, brominations are effected with N-bromosuccinimide (NBS) or other suitable N-bromo amides in the presence of catalytic quantitites of benzoyl peroxide, the reaction preferably run in CCl₄ (carbon tetrachloride) as solvent. Preparation of the reactants of formula 3 wherein Q is OH may be effected directly from (6) by reaction with CeAmNO₃ (ceric ammonium nitrate) or by converting the benzyl bromide (7) to its acetate followed by hydrolysis of the acetate with catalytic amounts of sodium methoxide in methanol, said reaction using standard procedures well known in the art.

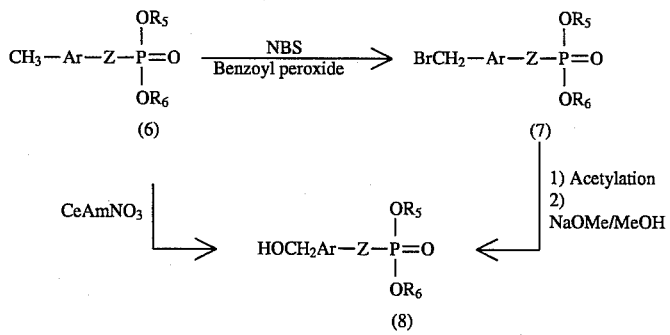

wherein Ar, Z, $R_5$ and $R_6$ are as previously defined except that $R'_4$ is a silyl ether (instead of OH) and $R_9$ is a protected hydroxy group rather than OH (if appropriate).

Once condensation of the 6-chloro purine base (2) is effected to produce compounds of formula Ia, the modifications at the 8,6- and/or 2-positions may be effected in a stepwise fashion to produce the desired $R_1$, $R_2$ and $R_3$ moieties of formula I.

To prepare compounds of formula I wherein both $R_5$ and $R_6$ are H and $R_1$ is OH, the corresponding phosphonate di-esters of Ia (i.e. $R_5$ and $R_6$ are alkyl) are successively reacted with trimethylsilylbromide (TMSBr) in CH₂Cl₂, water in acetonitrile and finally in HCl (1N) at 90° C. To prepare a monoester ($R_5$ is H and $R_6$ is alkyl) and $R_1$ is OH, the compounds of Ia are submitted directly to HCl/H₂O hydrolysis at 90° C.

To prepare compounds of formula I wherein $R_1$ is SH, compounds of formula Ia are reacted with thiourea in acetic acid. De-etherification of the resulting 6-SH products by treatment with TMSBr and hydrolysis will yield compounds wherein $R_1$ is SH and $R_5$ and $R_6$ are H.

To prepare the compounds of formula I wherein $R_1$ is SH, $R_2$ and $R_3$ are as defined (formula I) and $R'_4$ is H or a silyl ether (—O—SiMe₃), the corresponding 6-OH analog is reacted with dimeric phosphorous pentasulfide. The resulting compounds wherein $R'_4$ is a silyl ether can be converted to its alcohol and, if desired, the alcohol can be oxidized to its keto analog by methods described herein. The same reactants (except that $R_3$ is H) can be utilized to prepare compounds of formula I wherein $R_3$ is NH₂ or —NH—NH₂ by halogenation (at the 8-position of the purine moiety) using a brominating or iodinating agent such as bromine in water, a N-bromo or N-iodo imide (e.g. 1,3-dibromo-5,5-dimethyl-hydantoin, 1,3-diiodo-5,5-dimethyl-hydantoin, N-iodoacetamide, preferably NBS or NIS, and most preferably N-bromoacetamide (NBA). The so produced 8-halo analogs is reacted with hydrazine in a suitable solvent (e.g., water, ether, THF, p-dioxan, lower alkanols, ethylene glycol, chlorinated hydrocarbons (CCl₄, CH₂Cl₂), DMF, HMPA or DMSO at temperatures of about 50°–100° C., preferably but not necessarily using 2 to 3 fold excess of hydrazine. The corresponding 8-NH₂ compounds may be prepared by reducing the hydrazine using Raney Nickel. The 8-halo analogs used for reaction with hydrazine may be utilized to prepare compounds wherein $R_3$ is OH by reacting the 8-halo compound with an alkali metal or alkaline earth metal salt of a benzyl alcohol (e.g., benzyl alcohol) followed by subsequent reduction of the intermediate with hydrogen gas at atmospheric pressure in the presence of a noble metal catalyst (e.g., Pd/C).

To visualize the concepts relating to the route of synthesis and to more readily teach the alternate pathways by which the compounds of sub-type (a) wherein $R_4$ is H and $R'_4$ is OH, or $R_4$ and $R'_4$ form the defined keto moiety, the following schematic is depicted.

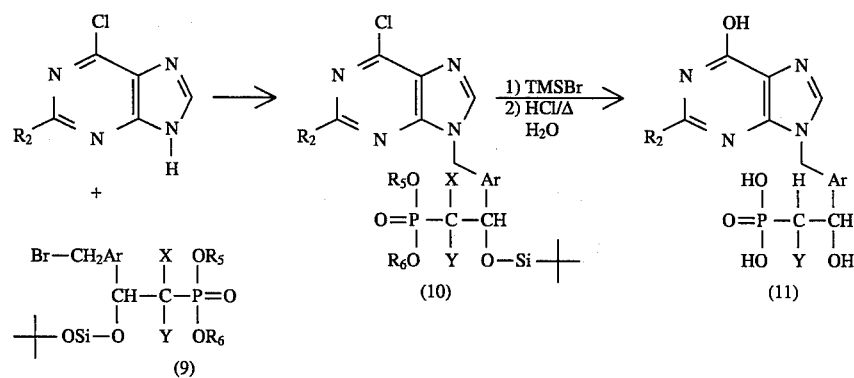

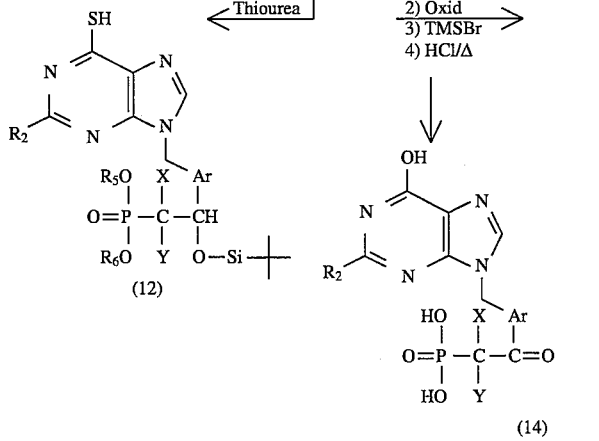

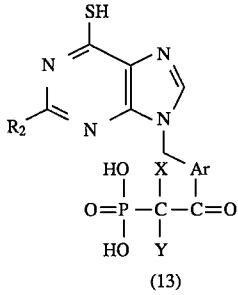

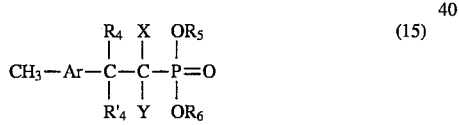

wherein

represents t-butyldimethylsilyl and Ar, X, Y, Bu₄NF, TMSBr being as previously defined. The preparation of the arylphosphonates of formula 6 may be effected using standard processes and techniques analogously known in the art; the particular route of synthesis, of course, being dependent on the definition of the Z moiety.

In the instance wherein it is desired to prepare intermediates of formula 6 wherein Z is represented by sub-type (a), i.e., compounds of formula $$\begin{array}{c} R_4 \; X \; OR_5 \\ | \; | \; | \\ CH_3-Ar-C-C-P=O \\ | \; | \; | \\ R'_4 \; Y \; OR_6 \end{array} \quad (15)$$

wherein Ar, R₄, R'₄, X, Y, R'₅ and R₆ are as described in formula I, the specific route of synthesis is primarily dependent on the specific definitions of R₄, R'₄, X and Y. In the instance wherein R₄ and R'₄ are hydrogen, the procedure is schematically represented as follows:

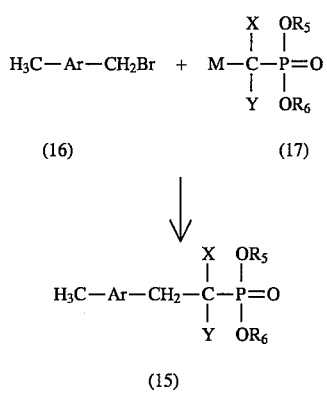

with M being Li, Na, —ZnBr, MgBr (preferably lithium) and X and Y are H, F or Cl. In this reaction the lithio derivative (17) prepared by reaction of the appropriate phosphonate with lithium di-isopropylamine (LDA) or butyl lithium, under an inert atmosphere (argon) in an anhydrous solvent (e.g. THF) at about −78° C. is condensed with the aryl bromide (16) by reaction for 10–20 hours and the reaction quenched with saturated aqueous ammonium chloride (NH₄Cl). Condensation of the reactants (16 and 17) wherein M is —ZnBr is preferably effected in the presence of catalytic amounts of copper bromide at 20° C. The Zn and Mg bromide derivatives are also prepared by standard processes.

In the instance wherein R₄ is H and R'₄ is OH or F, or R₄ and R'₄ form a keto moiety (as defined), the compounds are prepared as schematically illustrated as follows:

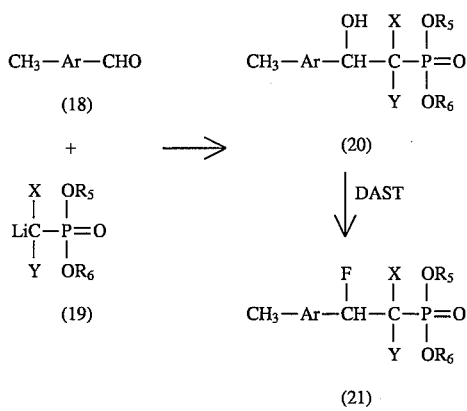

The reaction of the aldehydes (18) with the lithio derivative (19) is effected in THF at −78° C. under argon for about 3 hours and the reaction is then quenched with saturated aqueous NH₄Cl at about −78° C. to −30° C. to produce compounds (20). In treating compounds (20) with DAST (diethylamino sulfurtrifluoride) the reaction is run in dichloromethane at about 0° C. for about 15 to 25 hours and the reaction quenched using excess methanol. The alcohols (20) may also be oxidized to their keto forms by use of the Swern oxidation reaction using oxalyl chloride in DMSO) or by the use of tetrapropylammonium perruthenate and N-methyl morpholine N-oxide. Alternatively, the ketones may be formed directly from reaction of the compounds (19) (wherein M is Li or —ZnBr) with compounds of the formula

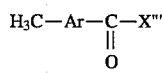

wherein X''' is chloro or alkoxy.

In effecting this latter reaction to prepare the ketones directly, it is specifically preferred that X''' be alkoxy (e.g., methoxy) and M be lithium when both X and Y are H, and when both X and Y are F it is specifically preferred that X''' be chloro and M be —ZnBr.

In the case wherein $R_4$ is H, $R'_4$ is OH or $R_4$ and $R'_4$ form the defined ketone, it is preferred that a silyl ether of compound (20) be utilized (e.g., a t-butyl dimethylsilyloxy derivative) as already described for the condensation of the reactants (2) and (3). These silyl derivatives are prepared by reacting compounds 19 with t-butyl dimethylsilyl chloride in the presence of imidazole and the resulting products activated with NBS. Selective removal of the silylprotecting group at a later stage is effected by treatment with tetrabutyl ammonium fluoride ($Bu_4NF$), as particularized above.

In the particular case when compounds of Ia are prepared wherein $R_4$ and $R'_4$ form the defined ketone and X and Y are H, it is preferred to utilize the following reaction scheme:

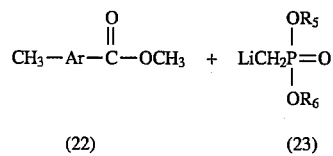

(22)        (23)

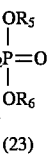

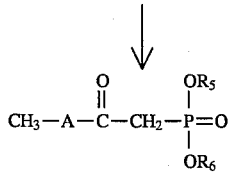

(24)

TBDMS.Cl/Imidazole

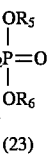

(25)

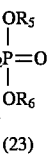

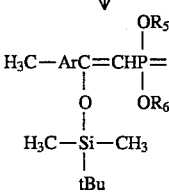

(26)

It should be noted that in the instance wherein it is desired to prepare compounds of Ia wherein Z is sub-type (a) by a condensation wherein Q of formula 3 is OH, and each of $R_4$, $R'_4$, X, and Y are H, it is preferred to reduce intermediates of sub-type (c) to obtain the appropriate reactants embraced within generic formula 3.

In the instance wherein it is desired to prepare intermediates embraced within formula 6 wherein Z is of sub-type (b), i.e., compounds of formula

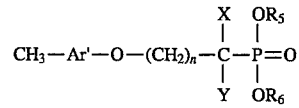

wherein Ar' is other than a furan or thiophene bridging moiety, standard procedures analogously known in the art may be utilized. In general, the intermediates are prepared according to the following reaction scheme:

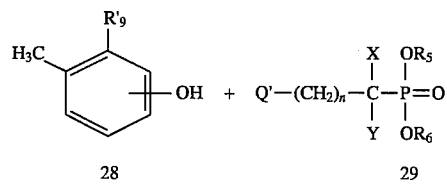

28                                29

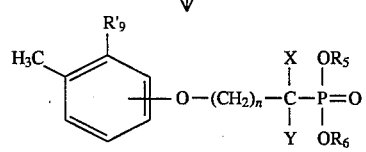

30 wherein $R'_9$ is as defined for $R_9$ in formula I other than OH, Q' is iodo, bromo, tosylate, mesylate or triflate leaving groups and n is an integer 1 to 5. The condensation is effected in the presence of a base (e.g., NaH, $K_2CO_3$ or KH) in a non-aqueous solvent (e.g., DMF, THF or DMSO) using standard procedures well known in the art. In the special instance wherein n is 2, the cresols (i.e., o, m, or p cresols) are reacted with ethylene carbonate in the presence of KF to obtain the benzoxy ethyl-1-ol-ether which is converted to its 1-bromo derivative by reaction with bromine in the presence of triphenyl phosphine ($P\phi_3$) in benzene in the presence of a base to afford the benzoxy ethyl bromide, by standard procedures is reacted with a lithio derivative of formula (17) to produce compounds (30a) wherein n is 2.

Of course, when n is zero and X and Y are both H, it is preferred to use the process wherein Q' is a tosylate (of compounds 29) using NaH as a base in DMF.

In those instances wherein it is desired to prepare compounds of formula 6 wherein Z is represented by sub-type (c), i.e., compounds of the formula $$CH_3-Ar-\underset{\underset{O}{\mid}}{C}=\underset{\underset{OR_6}{\mid}}{\overset{\overset{Y}{\mid}}{C}}-\overset{\overset{X}{\mid}}{\underset{}{P}}=O \quad 31$$

wherein Ar, X, Y, $R_5$ and $R_6$ are as defined as in formula I, said compounds may be prepared by methods and processes analogously known in the art.

In the instance wherein Y is H and X is H, F or Cl, an aryl aldehyde (32) is condensed with a lithio derivative of an X-substituted diphosphonate derivative (33) according to the reaction scheme:

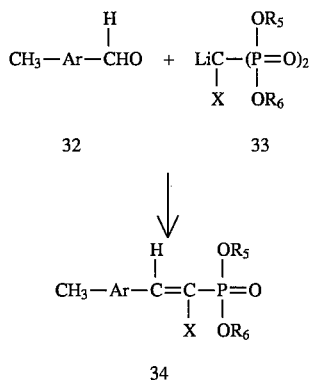

The reaction is conducted at −78° C. in THF and prior to quenching the mixture is allowed to warm to about 20° C. before hydrolysis with saturated aqueous NH₄Cl. When Y is F and X is H, F, or Cl, the preparation is effected using a compound of sub-type (a) (i.e., compound (35) wherein X' is F or Cl) which is treated with a base, preferably tBuOK, DBU of DMAP in a non-reactive solvent (DMF or DMSO) at temperatures of about 40° C. to 80° C. In this reaction the double bond is created by the loss of HX'. By choosing the appropriate analogs of compounds (35) and by following the foregoing treatment with a base, the desired Y and X compounds (34a) may be prepared when either HF or HCl is split off. The reaction is depicted as follows:

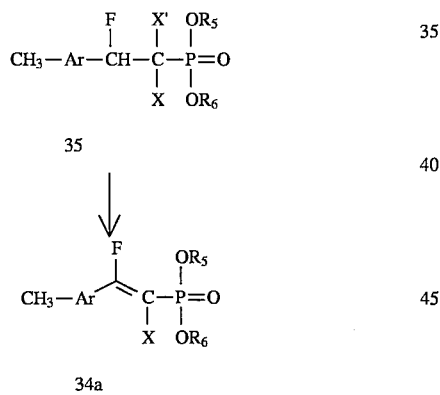

In the instance wherein it is desired to prepare intermediates of formula 6 wherein Z is represented by sub-typed (d), i.e., compounds of formula

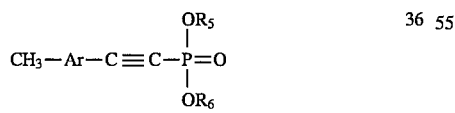

the compounds are prepared by treatment of compounds of formula (24) with two equivalents of DAST at 0° C. to 20° C. in CH₂Cl₂ for 1 to 5 hours and the reaction is quenched with excess methanol to yield the desired products 36.

In those instances wherein it is desired to prepare compounds of formula 6 wherein Z is represented by sub-type (e), i.e., compounds of the formula

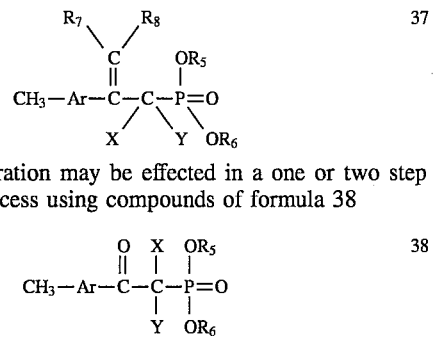

Their preparation may be effected in a one or two step olefination process using compounds of formula 38

In the one-step process a Wittig-type olefination process using a phosphonium ylide of the formula

reacted with a compound of formula 38 (especially when X and Y are F); the reaction being conducted in THF at −78° C. to 0° C. yield the double bond. Alternatively reactant 39 may be replaced with a reactant (40) of the formula $$\begin{array}{c} R_7 \\ \phantom{R_8}\diagdown \ominus \\ \phantom{R_8R_8}\text{Het} \\ R_8 \phantom{\diagdown} \end{array} \qquad 40$$

wherein Het is —Sø, SiMe3, Seø, —SMe or SeMe, and when reacted will produce compounds of formula (41)

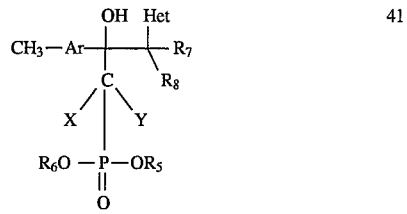

In those instances wherein Het is SiMe₃, the Peterson olefination is utilized using (a) treatment of 41 with NaH in DMF at 0° to 60° C. or (b) treatment of 41 with an acid, e.g., PTSA (p-toluenesulfonic acid) at elevated temperatures. When het is other than SiMe₃, treat 41 with SOCl₂, POCl₃ or PI₃ with Et₃N or pyridine in CH₂Cl₂ at temperature of about −20° to 20° C.

The following examples will illustrate the methods by which the compounds of this invention may be prepared.

SYNTHESIS OF 1

[2-[2-[(2-amino-1,6-dihydro-6-oxo-9H-purin-9-yl)methyl]phenyl]-1,1-difluoroethyl]phosphonic acid PREPARATION OF 1A:
[2-[2-methylphenyl]-1,1 -difluoroethyl]phosphonic acid, diethyl ester difluoroethyl]phosphonic acid, diethyl ester 30 mmol (5.64 g) of diethyl difluoromethane phosphonate dissolved in 30 ml of anhydrous tetrahydrofuran (THF) are slowly added to a stirred solution of (LDA) lithium diisopropylamide (prepared at 0° C. from 31 mmol of n-butyllithium and 30 mmol of diisopropylamine in 30 ml of anhydrous THF) at −78° C. under argon. After 30 minutes, 45 mmol (8.33 g) of 2-bromo-o-xylene are added to the reaction mixture which is stirred at −78° C. for 15 hours and quenched by adding 20 ml of an aqueous saturated solution of ammonium chloride. The crude mixture is evaporated to dryness; the residue is suspended in 50 ml of water and extracted 3 times with 100 ml of ethylacetate. The organic layers are dried over sodium sulfate, filtered and evaporated to give approximately 8 g of crude product which is purified by flash chromotography on silica gel affording 3.6 g of 1A (41% yield).

PREPARATION OF 1B:
[2-[2-[(2-amino-1,6-dihydro-6-chloro-9 H-purin-9-yl)methyl]phenyl]-1,1,difluoroethyl] phosphonic acid, diethyl ester N-bromo-succinimide (3 mmol, 0.53 gr) and benzoyl peroxide (5 mg) are added to a solution of 1A (3 mmol, 0.88 g in 20 ml of carbon tetrachloride). The mixture is refluxed, by heating with a lamp for 90 minutes, until all solid succinimide is apparent. The reaction mixture is filtered to remove succinimide and the filtrate is evaporated to dryness to give 1.1 g of an oil which is then added to a stirred solution of the sodium salt of 6-chloroguanine (prepared in 5 ml DMF by adding 3,2 mmol of sodium hydride to 3.9 mmol of 6-chloroguanine at 20° C. under argon). The reaction mixture is stirred at 20° C. for 20 hours, evaporated under reduced pressure and purified by flash chromotography on silica gel giving 1.15 g of expected 1B (42%).

PREPARATION OF 1:
[ 2-[2-[(2-amino-1,6 -dihydro-6-oxo-9H-purin-9-yl)methyl]phenyl]-1,1 -difluoroethyl]phosphonic acid 4 mmol (0.5 ml) of trimethylsilylbromide (TMSBr) are added to a stirred solution of 1C (0.6 g; 1.3 mmol) in 5 ml of anhydrous dichloromethane at 20° C. under argon. The reaction mixture is stirred for 20 hours and 0.5 ml of TMSBr is added to the reaction mixture. After 20 hours, the reaction mixture is evaporated; the residue is dissolved in 3 ml of acetonitrile and quenched with approximately 0.2 ml of water.

The mixture is evaporated and the residue is heated in 7 ml of 1N HCl at 100° C. for 20 hours. The mixture is evaporated and the product is obtained after 2 recrystallizations from hot water: 200 mg (38% yield; mother liquors contain essentially pure product for subsequent isolation.)

SYNTHESIS OF 2

[2-[2-[(2-amino-1,6-dihydro-6-oxo-9H-purin-9-yl)-methyl]phenyl]-1-fluoroethenyl]phosphonic acid PREPARATION OF 2A:
[2-(2-methylphenyl)-1-fluoroethenyl]phosphonic acid, diethyl ester 20 mmol (6.72 g) of bis(diethylphosphonyl)fluoromethane dissolved in 20 ml of anhydrous THF are slowly added to a −78° C. solution of lithium diisopropylamide (prepared by adding 22 mmol of n-butyllithium to a solution of 22 mmol of diisopropylamine in 16 ml of THF at 0° C.). After 30 minutes at −78° C., a solution of 30 mmol (3.5 ml) of freshly distilled o-tolualdehyde in 20 ml of THF is added to the reaction mixture which is stirred at −78° C. for 3 hours and at 20° C. for 5 hours, quenched with 20 ml of aqueous saturated ammonium chloride and evaporated to dryness. The residue is suspended in 30 ml of water and extracted three times with 100 ml of ethylacetate. The organic layers are washed with brine, dried over sodium sulfate, filtered, and evaporated to give 5 g of crude material which is purified by flash chromatography on silica gel affording 70 mmol (50%) of 2A.

PREPARATION OF 2D:
[2-[2-(2-amino-1,6-dihydro-6-chloro-9H-purin-9-yl)methyl]phenyl]-1-fluoroethyenyl]phosphonic acid, diethyl ester Benzoyl peroxide (10 mg) is added to a suspension of NBS (10 mmol) and 2A (10 mmol) in 15 ml of anhydrous carbon tetrachloride. The mixture is heated to reflux with a lamp until all solid is floating up. The reaction mixture is filtered and evaporated to give 2C as an oil which is then dissolved in 4 ml of anhydrous DMF and added to a stirred solution of the sodium salt of 6-chloro-guanine (prepared by adding 10 mmol of NaH (as a 60% solution w/v) to 10 mmol of 6-chloro-guanine in 10 ml of anhydrous DMF at 20° C. under argon). After 20 hours at 20° C., the reaction mixture is evaporated to dryness and the crude residue is directly purified by flash chromatography on silica gel giving 4 mmol of product 2D (40% yield).

PREPARATION OF 2:
[2-[2-[(2-amino-1,6-dihydro-6-oxo-9 H-purin-9-yl)methyl]phenyl]-1-fluoroethenyl] phosphonic acid The preparation of 2 from 2D was performed using the procedure already described for the transformation of 1C into 1.

SYNTHESIS OF 3

[2-[2-[(2-amino-1,6-dihydro-6-oxo-9H-purin-9-yl) methyl]phenyl]-1,1,2-trifluoroethyl]phosphonic acid PREPARATION OF 3A:
[2-hydroxy-2-(2-methylphenyl]1-difluoro-ethyl]phosphonic acid, diethyl ester 42.5 mmol of diethylphosphinyl difluoromethane (8 g) dissolved in 42 ml of anhydrous THF are slowly added to a stirred solution of freshly prepared lithium diisopropylamide (42.5 mmol) in 40 ml of THF at −78° C. under argon. The reaction mixture is stirred at −78° C. for 35 minutes and 7.65 g of o-tolualdehyde (63.75 mmol) dissolved in 42 ml of THF are added to the reaction mixture which is stirred at −78° C. for 4 hours, quenched at −78° C. by addition of 40 ml of saturated aqueous ammonium chloride* and evaporated under reduced pressure. The residue is suspended in water and extracted three times with 200 ml portions of ethyl acetate. The organic layers are washed with brine, dried over sodium sulfate, filtered, evaporated and purified by flash chromatography on silica gel to give 10.67 g of 3A as white crystals (81% yield)

PREPARATION OF 3B:
[2-fluoro-2-[2-methylphenyl]-1,1 -difluoroethyl]phosphonic acid, diethyl ester 2.3 ml of diethylamino sulfur trifluoride (DAST) are added dropwise to a stirred solution of 3A (4.6 g; 15 mmol) in 20 ml of anhydrous dichloromethane at 20° C. under argon. After two hours at 20° C., the reaction mixture is slowly quenched at 0° C. with excess methanol (5 ml), evaporated to dryness and directly purified by flash chromatography on silica gel to give 4.22 g of product 3B (91% yield).

PREPARATION OF 3C:
[2-[2-[(2-amino-1,6 -dihydro-6-chloro-9H-purin-9-yl)Methyl]phenyl]-1,1,2-trifluoroethyl] phosphonic acid, diethyl ester The bromination reaction of 3B and subsequent condensation with 6-chloroguanine was run exactly as described for the preparation of 1C from 1B.

PREPARATION OF 3:
[2-[2-[(2-amino-1,6-dihydro-6-oxo-9 H-purin-9-yl)methyl]phenyl]-1,1,2-trifluoroethyl] phosphonic acid Final product 3 was isolated after deprotection with TMSBr/$CH_2Cl_2$ and 1N HCl in water as described for the preparation of 1 from 1C.

SYNTHESIS OF 4

[2-[2-[(2-amino-1,6-dihydro-6-oxo-9H-purin-9-yl)-methyl]phenyl]-2-hydroxy-1,1-difluoroethyl] phosphonic acid

PREPARATION OF 4A:
[2-(t-butyldimethylsilyloxy)-2-(2 -methyl-phenyl)-1,1-difluoroethyl]phosphonic acid, diethyl ester Diethylphosphinyl difluoromethane (4.7 g, 25 mmol) dissolved in 25 ml of anhydrous THF is added dropwise to a −78° C. solution of lithium diisopropylamide (LDA) (prepared by reacting 25 mmol of n-butyllithium with 25 mmol of diisopropylamine at 0° C. in 25 ml of THF) under argon. After minutes at −78° C., a solution of o-tolualdehyde (30 mmol, 3.6 g) in 20 ml of anhydrous THF is added to the reaction mixture. After 3 hours at −78° C., 30 mmol of t-butyldimethylsilylchloride are added to the reaction mixture which is stirred at −20° C. for 2 hours, quenched with 10 ml of water, evaporated, extracted 3 times with 120 ml portions of ethylacetate. The organic layers are gathered, dried over sodium sulfate, filtered, evaporated and purified by flash chromatography on silica gel to give 8.8 g of product 4A (21 mmol, 84% yield).

PREPARATION OF 4B:
[2-(2-amino-1,6-dihydro-6-oxo-9H-purin-9-yl)methyl] phenyl]-[2-(t-butyldimethylsilyloxy)-1,1-difluoroethyl]phosphonic acid, diethyl ester The preparation of 4B from 4A was performed using the procedure already described for the transformation of 1A into 1C.

PREPARATION OF 4C:
[2-[2-amino-1,6-dihydro-6-oxo-9H-purin-9-yl)methyl] phenyl]-2-hydroxy-1,1-difluoroethyl]phosphonic acid, diethyl ester 12 mmol (3.85 g) of tetrabutyl ammonium fluoride are added in one portion to a stirred solution of 4B (6 mmol) dissolved in 150 ml of THF. The reaction mixture is stirred at 20° C. for 20 hours, evaporated to dryness and purified by flash chromatography on silica gel giving 4.8 mmol of 4C (80% yield).

PREPARATION OF 4:
[2-[2-[(2-amino-1,6-dihydro-6-dihydro-6-oxo-9 H-purin-9-yl)methyl]phenyl]-2-hydroxy-1,1-difluoroethyl]-phosphonic acid Compound 4 was obtained from 4C by the two chemical deprotection steps (TMSBr); $H_3O^+$) already described.

SYNTHESIS OF 5

[2-[2-[(2-amino-1,6-dihydro-6-oxo-9H-purin-9-yl) methyl]-phenyl]-2,2-dihydroxy-1,1-difluoroethyl]phosphonic acid

PREPARATION OF 5A FROM 4C:
[2-[2-(2-amino-1,6-dihydro-6 -oxo-9H-purin-9-yl)methyl]phenyl]-2-hydroxy-1,1, difluoroethylphosphonic acid, diethyl ester 60 mmol (4.3 ml) of DMSO dissolved is 25 ml of anhydrous dichloromethane are added dropwise at −65° C. to a stirred solution of 30 mmol of oxalylchloride (26 ml) in 25 ml of anhydrous dichloromethane under argon. The reaction mixture is stirred at −65° C. for 5 minutes and 20 mmol of 4C dissolved in 25 ml of $CH_2Cl_2$ are added. The reaction flask is removed from the cooling bath for a few minutes and the mixture is stirred again at −65° C. for 15 minutes. At that time, 100 mmol (13.8 ml) of triethylamine are added to the reaction mixture which is stirred for 10 minutes at −65° C, quenched with aqueous citric acid, stirred a few minutes at 20° C., extracted with dichloromethane (3 times with 75 ml portions), washed with brine, dried over $Na_2SO_4$, filtered, evaporated, and purified by flash chromatography on silica gel giving 13.5 mmol of product 4C (67%).

PREPARATION OF 5:
[2-[2-[(2-amino-1,6-dihydro-6-oxo-9H-purin-9-yl) methyl]phenyl]-2,2-dihydroxy-1,1-difluoroethyl]phosphonic acid Final product 5 is obtained from 5A by two deprotection steps performed as in the preparation of 1 from 1C.

SYNTHESIS OF 6

[3-[2-[(2-amino-1,6-dihydro-6-chloro-9H-purin-9-yl) methyl]phenoxy]-1,1-difluoropropyl]phosphonic acid

PREPARATION OF 6A:
3-(2-methylphenoxy)-1-propanol 300 mmol of ortho-cresol, 334 mmol of ethylene carbonate and 325 mmol of potassium fluoride are added to 100 ml of anhydrous DMF and stirred at 125° C. for 50 hours under argon. 40 mmol of ethylene carbonate and 40 mmol of KF are added to the reaction mixture which is then stirred for another 24 hours at 125° C.

The reaction mixture is cooled to 20° C., filtered, and evaporated. The residue is purified by flash chromatography on silica gel to give 38.6 g of expected product (85% yield).

PREPARATION OF 6B:
3-(2-methylphenoxy)-1-bromopropane 10 g of bromine (62.5 mmol) dissolved in 30 ml of benzene (or acetonitrile) are slowly added to a stirred solution of triphenylphosphine (64 mmol) in 100 ml of benzene (or acetonitrile). After 15 minutes, triethylamine (64 mmol) dissolved in 35 ml of benzene (or acetonitrile) is added to the reaction mixture followed by addition of the starting material 6A (9.68 g; 63.7 mmol) dissolved in 50 ml of benzene (or acetonitrile). The reaction mixture is stirred at 20° C. for 20 hours, filtered (to removed most of the triphenylphosphine oxide), evaporated, and purified by flash chromatography on silica gel to give 9.8 g of expected product.

PREPARATION OF 6C:
[3-(2-methylphenoxy)-1,1-difluropropyl]phosphonic acid, diethyl ester 30 mmol (5.64 g) of difluoromethyl O,O-diethylphosphonate dissolved in 30 ml of anhydrous THF are slowly added to a stirred solution of 37 mmol of LDA (prepared from 31 mmol of n-butyllithium and 31 mmol of diisopropylamine in 30 ml of THF) at −78° C. under argon. The reaction mixture is stirred at −78° C. for 30 min and the starting material 6B (20 mmol) dissolved in 10 ml of anhydrous THF is added to the reaction mixture. Stirring is continued for 3 hours at −78° C.; the temperature is slowly raised to 20° C., and the reaction mixture is quenched with saturated aqueous ammonium chloride. The crude mixture is then evaporated and extracted with ethylacetate. The organic layers are gathered, washed with water and brine, dried over sodium sulfate, filtered, evaporated, and purified by flash chromatography on silica gel to give 40% (16 mmol) of the expected condensation product.

PREPARATION OF 6D:
[3-[2-[(2-amino-1,6-dihydro-6-chloro-9 H-purin -9-yl)methyl]phenoxy]-1,1-difluropropyl]phosphonic acid, diethyl ester 6 mmol of starting material 6C dissolved in 15 ml of anhydrous carbon tetrachloride are heated with a lamp with 6 mmol of N-bromosuccinimide and a few milligrams of benzoylperoxiole during 35 minutes. The crude mixture is filtered to remove succinimide and the filtrate is evaporated to dryness, dissolved in 8 ml of anhydrous DMF and stirred at 20° C. under argon with 6.5 mmol of 6-chloroguanine and 13 mmol of potassium carbonate for 24 hours. The mixture is evaporated to dryness and the residue is suspended in 50 ml ethylacetate, washed with ammonium chloride and brine, dried over sodium sulfate, filtered, evaporated, and purified by flash chromatography on silica gel to give 3 mmol of the expected product.

PREPARATION OF 6:
[3-[2-[(2-amino-1,6-dihydro-6-chloro-9 H-purin-9-yl)methyl]phenoxy]-1,1-difluoropropyl]phosphonic acid 9 mmol of freshly distilled TMSBr are slowly added to a stirred solution of starting material 6D (3 mmol) dissolved in 10 ml of anhydrous dichloromethane at 20° C. under argon. The reaction mixture is stirred at 20° C. for 20 hours and evaporated to dryness. The residue is dissolved in 8 ml of anhydrous acetonitrile and quenched with 10 mmol of water. A white precipitate is formed which is separated by filtration and collected to give the expected product which is used without further purification in the next step.

2 mmol of starting material dissolved in 10 ml of 1N HCl and 2 ml of THF are heated at 90°–100° C. for 20 hours. The reaction mixture is cooled to 20° C., evaporated to dryness, dissolved in saturated aqueous triethylammonium bicarbonate, filtered and crystallized by addition of 1N HCl.

The white solid is collected, dried under reduced pressure to give 1.7 mmol of expected product as the hemihydrate.

SYNTHESIS OF 7

[2-[(2-amino-1,6,dihydro-6-oxo-9H-purin-9yl) methyl]phenoxy]methylphosphonic acid PREPARATION OF 7A: 2-methylphenoxymethyl phosphonic acid, diethyl ester Sodium hydride (8 mmol of a 60% suspension in oil) is added to a stirred solution of o-cresol (8 mmol, 864 mg) in 10 ml of anhydrous DMF at 20° C. under argon. After 45 minutes, the O,O-diethyl methyl phosphonate tosylate derivative (8 mmol, 2.54 g) dissolved in 3 ml of DMF is added to the reaction mixture which is stirred at 60° C. for 20 hours, evaporated under reduced pressure and purified by flash chromatography on silica gel to give 1.1 g of product (69% yield).

PREPARATION OF 7B:
[2-[(2-amino-1,6, dihydro-6-chloro-9 H-purin-9yl)methyl]phenoxy]methylphosphonic acid, diethyl ester The phosphonate 7A (1.03 g, 4 mmol), N-bromosuccinimide (4.2 mmol; 743 mg) and a few milligrams of benzoyl peroxide in 10 ml of $CCl_4$ are heated to reflux under a heating lamp. After 35 minutes, the reaction mixture is filtered and evaporated to give 1.3 g of an oil which is dissolved in 3 ml of anhydrous DMF and added to a stirred suspension of 6-chloroguanine (4.4 mmol; 745 mg) and potassium carbonate (10 mmol; 1.38 g) in 6 ml of anhydrous DMF at 20° C. under argon. After 40 hours, the reaction mixture is evaporated under reduced pressure and purified by flash chromatography on silica gel giving 1.25 g of expected product (74% yield).

PREPARATION OF 7:
[2-[(2-amino-1,6,dihydro-6-oxo-9H-purin-9yl)methyl]phenoxy]methylphosphonic acid By chemical deprotection using TMSBr and then aqueous hydrolysis performed as already described one obtains the title compound.

SYNTHESIS OF 8

[2-[2-[(2-amino-1,6-dihydro-6-oxo-9H-purin-9-yl) methyl]phenyl]1,1-difluoro-2-propenyl]phosphonic acid PREPARATION OF 8A:
[2-[2-methylphenyl]1,1 difluorooxoethyl]-phosphonic acid, diethyl ester 50 mmol (13,35 g) of O,O-diethylbromodifluoromethane phosphonate dissolved in 50 ml of dimethoxyethane (DME) are slowly added to a stirred suspension of freshly activated zinc (55 mmol) in 15 ml of DME at such a rate that a gentle reflux is maintained. The reaction mixture is stirred at 20° C. for 2 hours and 60 mmol of o-toluic acid chloride (25 g) dissolved in 15 ml of DME are added to the reaction mixture which is stirred at 20° C. for 20 hours. The crude material is filtered over celite and the filtrate is evaporated to dryness and directly purified by flash chromatography on silica gel giving 30 mmol of product 8A (60%).

PREPARATION OF 8B:
[2-[2-methylphenyl]1,1 difluoro-2-propenyl]phosphonic acid, diethyl ester 35 mmol of n-butyllithium (21.8 ml of 1.6N solution in hexene) are slowly added to a stirred suspension of 35 mmol of methyl triphenylphosphonium bromide in 50 ml of THF at −78° C. under argon. The reaction mixture is stirred for 2 hours at 0° C., and 30 mmol of compound 8A dissolved in 30 ml of THF are added to this reaction mixture at −78° C. After stirring at −78° C. for 2 hours and at 0° C. for 2 hours, the reaction mixture is hydrolyzed with saturated aqueous ammonium chloride. The crude product is evaporated under reduced pressure and extracted 3 times with 100 ml of ethyl acetate. Usual work-up and purification by flash chromatography on silica gel affords 18 mmol of 8B (60% yield).

PREPARATION OF 8C:
[2-[2-[(2-amino-1,6-dihydro-6-chloro-9 H-purin-9-yl)methyl]phenyl]1,1 difluoro-2-propenyl]phosphonic acid, diethyl ester The bromination reaction of 8B and subsequent condensation with 6-chloroguanine was run exactly as described for the preparation of 1C from 1B.

PREPARATION OF 8:
[2-[2-[(2-amino-1,6-dihydro-6-oxo-9 H-purin-9-yl)methyl]1,1 difluoro-2-propenyl]phosphonic acid Final product 8 was isolated from 8C after deprotection with TMSBr/CH$_2$Cl$_2$ and 1N HCl in water as described for the preparation of 1 from 1C.

SYNTHESIS OF 9

[2-[2-[(2-amino-1,6-dihydro-6-oxo-9H-purin-9-yl)methylphenyl]ethynyl]phosphonic acid

PREPARATION OF 9A:
[2-[2-methylphenyl]-2-oxoethane phosphonic acid, diethyl ester 100 mmol of n-butyllithium are slowly added to a stirred solution of 100 mmol of methyl phosphonic acid, diethyl ester dissolved in 100 ml of THF at −78° C. under argon. The reaction mixture is stirred at −78° C. for 2 hours and 50 mmol of o-toluene acid methyl ester dissolved in 50 ml of THF are added to the reaction mixture which is stirred at −78° C. for 20 hours and at 0° C. for 2 hours before being hydrolyzed by saturated aqueous ammonium chloride. Usual work-up and flash chromatography on silica gel affords 45 mmol (90% yield) of product 9A.

PREPARATION OF 9B:
[2-[2-methylphenyl]ethynylphosphonic acid, diethyl ester 61 mmol (8 ml) of diethylamino sulfurtrifluoride (DAST) are slowly added to a solution of 30 mmol of 9A in 50 ml of anhydrous dichloromethane at 0° C. The reaction mixture is stirred at 20° C. for 30 hours, and slowly quenched with excess methanol (5 ml) at 0° C. The reaction mixture is evaporated to dryness and directly purified by flash chromatography on silica gel giving 24 mmol of product 9B (80% yield).

PREPARATION OF 9C:
[2-[2-[(2-amino-1,6-dihydro-6-chloro-9 H-purin-9-yl)methyl]phenyl]ethynyl]phosphonic acid, diethyl ester The bromination reaction of 9B and subsequent condensation with 6-chloro-guanine was run exactly as described for the preparation of 1C from 1B.

PREPARATION OF 9:
[2-[2-[(2-amino-1,6-dihydro-6-oxo-9 H-purin-9-yl)methylphenyl]ethynyl]phosphonic acid 20 mmol (2,5 ml) of TMSBr are added to a stirred solution of 9C (5 mmol) in 25 ml of anhydrous dichloromethane at 20° C. under argon. The reaction mixture is stirred for 20 hours and evaporated under reduced pressure. The residue is dissolved in 20 ml of acetonitrile and a white solid is precipitated by addition of 0.5 ml of water. The white solid is collected by filtration and dissolved in a mixture of 15 ml of 0.2H HCl and 6 ml of THF. This solution is heated at 60° C. for 8 hours and the final product 9 is obtained after crystallization on cooling (1.4 mmol, 28% yield).

SYNTHESIS OF 10

2-2-[(2-amino-1,6-dihydro-6-oxo-9H-purin-9-yl) methylphenyl]ethenyl]phosphonic acid

PREPARATION OF 10A:
[2-[2-methylphenyl]-ethenyl]phosphonic acid, diethyl ester 38 mmol (10.95 g) of bis(diethylphosphonyl)methane dissolved in 25 ml of anhydrous tetrahydrofuran are slowly added to a suspension of NaH (42 mmol) in 20 ml of anhydrous tetrahydrofuran, at −15° C., under argon. After 45 minutes, 38 mmol (4.6 g) of o-tolualdehyde dissolved in 40 ml of tetrahydrofuran are added to the reaction mixture at 0° C. After stirring at 20° C. for 18 hours, the crude reaction mixture is quenched with 20 ml of aqueous saturated ammonium chloride and evaporated to dryness. The residue is suspended in 35 ml of water and extracted three times with 100 ml of ethyl acetate. The organic layers are washed with brine, dried over sodium suflate, filtered and evaporated to give 11 g of crude material which is purified by flash chromatography on silica gel affording 7.53 g of product 10A (75% yield).

PREPARATION OF 10B:
[2-[2-[(2-amino-1,6-dihydro-6-chloro-9H-purin-9-yl)methyl]phenyl]ethenyl]phosphonic acid, diethyl ester Benzoyl peroxide (20 mg) is added to a suspension of N-bromosuccinimide (20 mmol) and [2-[2-methylphenyl]-ethenyl] phosphonic acid, diethyl ester (20 mmol) in 15 ml of anhydrous carbon tetrachloride. The mixture is heated to reflux with a lamp until all solid is floating up. The reaction mixture is filtered and evaporated to give an oil which is then dissolved in 10 ml of anhydrous dimethylformamide and added to a stirred solution of the sodium salt of 6-chloroguanine (prepared by adding 20 mmol of NaH to 20 mmol of 6-chloro-guanine in 10 ml of anhydrous dimethylformamide at 20° C. under argon. The reaction mixture is stirred for 20 hours at 20° C., evaporated to dryness and the crude residue is directly purified by flash chromatography on silica gel giving 12 mmol of product 10B (60% yield).

PREPARATION OF 10:
[2-[2[(2-amino-1,6-dihydro-6-oxo-9H-purin-9-yl) methylphenyl]ethenyl]phosphonic acid, The preparation of 10 from 10B is performed using the procedure already described for the transformation of 1B to 1 of Synthesis 1.

BIOLOGICAL USEFULNESS

The ability of the compounds of this invention to act as immunosuppressant, antilymphoma, antileukemic, antiviral, and antiprotozoal agents and as agents useful in the treatment of gout, psoriasis and autoimmune diseases can be demonstrated by their ability to inhibit purine nucleoside phosphorylase (PNP). Purine nucleoside phosphorylase (PNP) inhibitory activity can be determined by the coupled xanthine oxidase method of Kalckar, using inosine as the substrate [H. M. Kalckar, J. Biol. Chem. 167, 429–443 (1947)]. Apparent dissociation constants ($K_i$) were measured at 1 mM inorganic phosphate using 0.1M HEPES buffer (pH 7.4), four concentrations of inosine ranging from 0.05 mM to 0.15 mM and various concentrations of inhibitor. The $K_i$ for representative members of the compounds of formula 1 are tabulated in table 1 and are compared to the $K_M$ values of the substrate inosine using PNP from various sources. Moreover, compounds of this invention have been shown to be effective against lymphomas (human MOLT-4 cells) and thus have antilymphomic and antileukemic activities. The presence of 2'-deoxyguanosine (about 1–10 μM), a natural metabolite, appears to be important for activity against lymphoma cells in culture.

The term protozoa is intended to include those members of the subphyla Sarcomastigophora and Sprozoa of the phylum Protozoa. More particularly the term protozoa as used herein is intended to include those genera of parasitic protozoa which are important to man because they either cause which are important to man because they either cause disease in man or in his domestic animals. These genera are for the most part found classified in the superclass of Mastigophora of the subphylum Sarcomastigophora and the class of Telosporea of the subphylum Sporozoa in the classification according to Baker (1969). Illustrative genera of these parasitic protozoa include Histomonas, Trypanosoma, Giardia, Trichomonas, Eimeria, Isopora, Toxoplasma, and Plasmodium.

Indeed, a preferred embodiment of the present invention is the use of these compounds as antiprotozoal agents in the treatment of intestinal coccidia in commercial poultry. Intestinal coccidia infections are responsible for multi-million dollars loses to the poultry industry in the United States each year. Due to the rapid development of drug resistance by coccidia, and due to the relatively high toxicity of some of the drugs used in the treatment of coccidiosis, there is a need for effective coccidiostats that are non-toxic and to which intestinal coccidia do not develop rapid drug resistance.

Although the immune system is a major defense against substances which can cause disease, it cannot distinguish between helpful and harmful foreign substances and destroys both. It would be useful in many instances to have a means of regulating the immune system without harming the individual. The compounds of this invention exhibit such modulating or regulatory effects and have potential for use in the treatment of various immune disorders such as rheumatoid arthritis and lupus erythromatus.

Circulating antibodies and cellular immune responses play a role in the rejection of transplanted tissues and organs.

| | $K_i$ (M) | | | |
| | PNP SOURCE | | | |
| Compound | Bovine Spleen | Rat Erythrocytes | Human Erythrocytes | E. Coli |
| --- | --- | --- | --- | --- |
| [2-[2-[(2-amino-1,6-dihydro-6-oxo-9H-purin-9-yl)methyl]phenyl]-1,1,difluoroethyl]phosphonic acid | $4 \times 10^{-9}$ | $2 \times 10^{-9}$ | $13 \times 10^{-9}$ | $15 \times 10^{-9}$ |
| [2-[2-[(2-amino-1,6-dihydro-6-oxo-9H-purin-9-yl)methyl]phenyl]-1-fluoroethenyl]phosphonic acid | $8 \times 10^{-10}$ | $4 \times 10^{-10}$ | $1.8 \times 10^{-9}$ | $2.5 \times 10^{-10}$ |
| [2-[2-[(2-amino-1,6-dihydro-6-oxo-9H-purin-9-yl)methyl]phenyl]-fluoroethenyl]phosphonic acid | — | — | $3.2 \times 10^{-9}$ | $5 \times 10^{-10}$ |
| [2-[2-[(2-amino-1,6-dihydro-6-oxo-9H-purin-9-yl)methyl]phenyl]-1,1,2-trifluoroethyl]phosphonic acid | $6 \times 10^{-10}$ | $5 \times 10^{-10}$ | $1.3 \times 10^{-9}$ | $7 \times 10^{-10}$ |
| [2-[2-[(2-amino-1,6-dihydro-6-oxo-9H-purin-9yl)methyl]pheno x y]-1,1-difluoropropyl]phosphonic acid | $2.5 \times 10^{-7}$ | $3.7 \times 10^{-8}$ | $2.1 \times 10^{-7}$ | — |
| [2-[(2-amino-1,6-dihydro-6-oxo-9H-purin9yl)methyl]pheno x y]methylphosphonic acid | $7.5 \times 10^{-9}$ | $7.3 \times 10^{-9}$ | $7.9 \times 10^{-8}$ | $4.5 \times 10^{-9}$ |
| inosine | $3 \times 10^{-5}$ | $1.5 \times 10^{-4}$ | $1.5 \times 10^{-4}$ | $8 \times 10^{-5}$ |

As used herein the term, patient, in regard to the suppression of immune system means mammals such as mice, rats, cats, dogs, cattle, sheep, swine, and primates including humans. The term, patient, in regard to the treatment of parasitic infections includes not only mammals but also other warm blood animals such as fowl including chickens and turkey.

Unless the donor is the identical twin of the recipient or is the individual himself, the recipient's lymphocytes recognize the transplant as "not self" and immediately respond to destroy it. The exceptions to this situation are transplants to non-vascularized areas (privileged sites), such as the cornea of the eye, where lymphocytes do not circulate and therefore are not sensitized and do not prompt an immune response. It is currently difficult to suppress the immune reaction to prevent rejection of the transplant without severely damaging the patient in other ways. The patient must also be given massive doses of antibiotics because his own defenses against infection have been suppressed. The compounds of this invention could be valuable in establishing tolerance to the transplant through controlled modulation of the immune system. In addition, these compounds demonstrate antiviral activities.

The amount of the active ingredient to be administered can vary widely according to the particular dosage unit employed, the period of treatment, the age and sex of the patient treated and the nature and extent of the disorder treated. The total amount of the active ingredient to be administered will generally range from about 1 mg/kg to 100 mg/kg and preferably from 3 mg/kg to 25 mg/kg. A unit dosage may contain from 25 to 500 mg of active ingredient, and can be taken one or more times per day. The active compound of formula 1 can be administered with a pharmaceutical carrier using conventional dosage unit forms either orally, parenterally, or topically. In a preferred mode, 2-deoxyguanosine will be administered conjunctively with a compound of this invention. Any effective nontoxic dose of 2-deoxyguanosine can be used, typically from about 0.5 to about 50 mg/kg per day will be administered. By conjunctively applicants contemplate not only those dosage forms which contain both 2-deoxyguanosine and a compound of formula 1, but also separate dosage forms. The compounds may also be administered in separate dosage units.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly-(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophilelipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

Aerosol or spray compositions containing the compounds of this invention can be applied to the skin or mucous membranes. Such compositions may contain a micronized solid or a solution of a compound of formula 1 and may also contain solvents, buffers, surfactants, perfumes, anti-microbial agents, antioxidants, and propellants. Such compositions may be applied by means of a propellant under pressure or may be applied by means of a compressible plastic spray bottle, a nebulizer, or an atomizer without the use of a gaseous propellant. A preferred aerosol or spray composition is a nasal spray.

The active ingredient may also be administered by means of a sustained release system whereby the compound of formula 1 is gradually released at a controlled, uniform rate form an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, an ocular insert placed in the cul de sac of the eye, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of formula 1. The unit dosage of the compound administered by means of a sustained release system will approximate the amount of an effective daily dosage multiplied by the maximun number of days during which the carrier is to remains on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as well as mixtures and copolymers of these polymers. The compounds of formula 1 may be incorporated in the sustained release carrier in a pure form or may be dissolved in any suitable liquid or solid vehicle, including the polymer of which the sustained release carrier is formed.

Another aspect of this invention is the use of the purine nucleoside phosphorylase inhibitors of formula I in conjunctive therapy to potentiate the efficacy of antiviral nucleoside analogs which would otherwise become subject to the enzymatic action of purine nucleoside phosphorylase.

In particular, this invention embraces the use of a compound of Formula I in conjunctive therapy for the treatment of retroviral infections, especially in humans, particularly human immunodeficiency virus. Particularly preferred 2', 3'-dideoxy purine nucleosides are 2'3'-dideoxyadenosine, 2', 3'-dideoxyguanosine, 2', 3'-dideoxythioinosine and 2', 3'-dideoxyinosine.

The potentiation of the anti-retroviral effect of a dideoxypurine nucleoside, e.g. of Formula I, by a PNP inhibitor can be determined, e.g. in cell cultures (e.g. H9 cells, ATH8 cells) exposed to a retrovirus (e.g. HIV) according to methodology well known in the art, such as described in Proc. Nat. Acad. Sci, U.S.A., 83, 1911 (1986). The potentiation can also be determined in vivo (e.g. in rats) by measuring the increase in the plasma level of the dideoxypurine nucleoside which is achieved by prior or simultaneous administration of the particular PNP inhibitor, according to methodology well known in the art.

The two active ingredients (2', 3'-dideoxypurine nucleoside and PNP inhibitors) may be administered simultaneously by the same or different routes, in the same or different formulations or may be administered at discrete points in time provided that there is effective PNP inhibition when the 2', 3'-dideoxypurine nucleoside is present. The extent to which this time separation of administered active agents can be accomplished depends upon the amount of available PNP and the rate at which the PNP inhibitor is itself degraded. For these reasons, the preferred dosage is in divided doses two to four times a day, most preferably with both agents being administered simultaneously.

It is known that purine nucleoside derivatives administered as antiviral agents are subject to a purine nucleoside phosphorylase catalysis which undesirably alters the efficacy of such agents. Indeed, the catalysis may lead to untoward side effects. It is also known that antiviral compounds which, per se, are not subject to purine nucleoside phosphorylase will, (either by mechanisms well understood e.g., enzymatic action of adenosine deaminase or by mechanisms not understood) become subject to the action of purine nucleoside phosphorylase, and thus the antiviral effectiveness of this type of compound will similarly be altered. Thus, for the purpose of this aspect of the invention both types of antiviral agents are embraced by the term antiviral agents subject to purine nucleoside phosphorylase.

This aspect of the invention may alternatively be expressed as: in the process for treating viral infections with antiviral agents subject to nucleoside phosphorylase, the improvement which comprises conjunctively administering a therapeutically effective amount of a purine nucleoside phosphorylase inhibitor, particularly those inhibitors embraced herein by those compounds embraced within the scope of the generic scope of formula I.

In this aspect of the invention, the term "antiviral" includes the treatment of viruses and diseases caused thereby—commonly known to be amenable to treatment with nucleoside analogs such as, for example, the HIV viruses imputed to be causative factors in AIDS, hepatitis B virus and herpes.

Particular antiviral agents of current interest for which enhanced antiviral efficacy would be achieved with conjunctive therapy with the PNPase inhibitors are such compounds as (a) dideoxy nucleosides of the formula

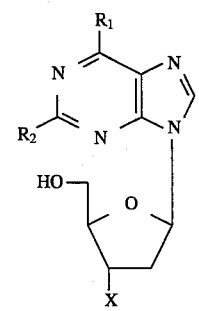

wherein

| $R_1$, $R_2$, X | Name | Target Virus |
|---|---|---|
| OH, H, H | dideoxyinosine | HIV |
| OH, $NH_2$, H | dideoxyguanosine | HIV, Hepatitis B |
| OH, $NH_2$, F | 3'-F-dideoxyguanosine | HIV |
| OH, $NH_2$, $N_3$ | 3'-azidodideoxyguanosine | HIV, Hepatitis B |
| $NH_2$, $NH_2$, H | dideoxydiamino purine riboside | HIV, HBV |
| $NH_2$, H, H | dideoxyadenosine | HIV |
| $NH_2$, $NH_2$, $N_3$ | 3'-azidodideoxydiaminopurine riboside | HIV, HBV |

The last three compounds are first substrates of adenosine deaminase, (b) dideoxy dehydro nucleosides of the formula

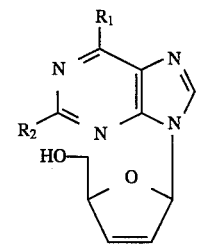

wherein

| $R_1$, $R_2$ | Name | Target Virus |
|---|---|---|
| OH, H | dideoxydehydro inosine | HIV |
| OH, $NH_2$ | dideoxydehydro guanosine | HIV |
| $NH_2$, H | dideoxydehydro adenine | HIV |

(c) dioxolane purine derivatives of the formula

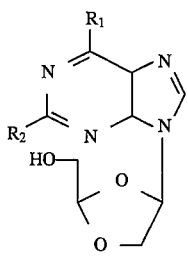

wherein the variations of $R_1$ and $R_2$ wherein $R_1$ is OH, or $NH_2$ and $R_2$ is H or $NH_2$, said compounds being targeted for HIV and HBV (i.e., hepatitis B), and (d) oxetane type derivatives of the formula

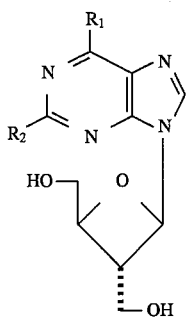

wherein $R_1$ is OH or $NH_2$ and $R_2$ is H or $NH_2$. The target viruses being HIV.

It is to be noted that the presently two best antiviral agents for hepatitis B (HBV) are dideoxyguanosine (ddGuo) and 2,6-diimino dideoxy purine riboside which is a "prodrug" of dideoxyguanosine.

Particularly useful compounds of this invention are the PNP inhibitors of the formula

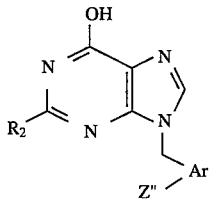

wherein $R_3$ is H, Ar is 2,3-thiophene, 2,5-furan or 3,4-furan, and Z" is $-CH_2CF_2-P(OH)_2$, and wherein Ar is 1,2-phenyl and $R_3$ is H or $NH_2$ and Z" is:
  $CH_2CF_2PO(OH)_2$,
  $CH_2CHFPO(OH)_2$,
  $CHFCF_2PO(OH)_2$,
  $CHOHCF_2PO(OH)_2$,
  $CH=CFPO(OH)_2$,
  $CH=CHPO(OH)_2$, or
  $COCF_2PO(OH)_2$.

As is true for most classes of chemo therapeutic agents, certain sub-generic and certain specific embodiments exhibit a more beneficial profile than others. In this class of PNP inhibitors of formula I those preferred compounds are compounds wherein $R_1$ is OH, $R_2$ is $NH_2$, $R_3$ is H or $NH_2$, Ar is 1,2-phenyl or 2,3-furan or thiophen, $R_5$ and $R_6$ are H. Preferred Z moieties are those of (a) wherein X and Y are F, $R_4$ is H and $R'_4$ is H or F, those of (b) wherein n is zero and X and Y are both H, those of (c) wherein X is F and Y is F or H, those of (d) wherein X is F and Y is F or H, those of (e) wherein X and Y are F and $R_7$ and $R_8$ are H. The preferred specific compounds are those final products of examples 1 to 10, as well as the 3-position amino analogs thereof.

What is claimed is:

1. A method of suppressing the immune system in a patient in need thereof which comprises administering to the patient a therapeutically effective amount of a compound of the formula

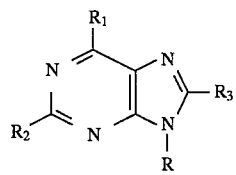

the tautomeric forms thereof, and the pharmaceutically acceptable salts thereof, wherein R is

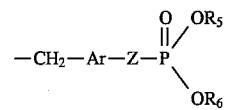

with Ar being a $R_9$-substituted phenyl, to which its adjacent $CH_2$ moiety is bonded to one ring carbon atom and the Z moiety is bonded to a second ring carbon atom of the Ar moiety, Z is a moiety selected from the group consisting of sub-types (a), (b), (c), (d), or (e) wherein (a) is

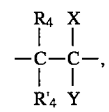

(b) is

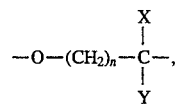

(c) is

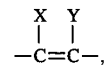

(d) is $-C\equiv C-$, and (e) is

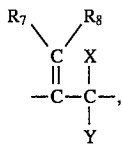

wherein n is an integer of 1 to 5 or zero;
$R_1$ is $-OH$ or $-SH$;
$R_2$ is H or $-NH_2$;
$R_3$ is H, $-NH_2$, $-OH$, or $-NH-NH_2$;
$R_4$ is H;

R'$_4$ is H, OH or F, or R$_4$ and R'$_4$, together with the carbon atom to which they are attached, form a keto moiety;

R$_5$ is C$_{1-6}$ alkyl or H;
R$_6$ is C$_{1-6}$ alkyl or H;
R$_7$ is H, F, or C$_{1-4}$ alkyl;
R$_8$ is H, F, or C$_{1-4}$ alkyl;
R$_9$ is H, Cl, Br, C$_{1-6}$ alkyl, C$_{1-6}$ alkoxy, OH, NH$_2$ or CH$_3$;

X and Y are H, F or Cl, with the proviso that when n is zero, X and Y are both H.

2. A method according to claim 1 wherein said compound is selected from the group consisting of
[2-[2-[(2-amino-1,6-dihydro-6-oxo-9H-purin-9-yl)methyl]phenyl]-1,1-difluoroethyl]phosphonic acid,
[2-[2-[(2-amino-1,6-dihydro-6-oxo-9H-purin-9-yl)methyl]phenyl]-1-fluoroethenyl]phosphonic acid,
[2-[2-[(2-amino-1,6-dihydro-6-oxo-9H-purin-9-yl)methyl]phenyl]-1,1,2-trifluoroethyl]phosphonic acid,
2-[2-[(2-amino-1,6-dihydro-6-oxo-9H-purin-9-yl)methyl]phenyl]-2-hydroxy-1,1-difluoroethyl]phosphonic acid,
[2-[2-[(2-amino-1,6-dihydro-6-oxo-9H-purin-9-yl)methyl]phenyl]-2,2-dihydroxy-1,1-difluoroethyl]phosphonic acid,
[3-[2-[(2-amino-1,6-dihydro-6-chloro-9H-purin-9-yl)methyl]phenoxy]-1,1-difluoropropyl]phosphonic acid,
[2-[(2-amino-1,6-dihydro-6-oxo-9H-purin-9-yl)methyl]phenoxy]methylphosphonic acid,
[2-[2-[(2-amino-1,6-dihydro-6-oxo-9H-purin-9-yl)methyl]phenyl]-1,1-difluoro-2-propenyl]phosphonic acid,
[2-[2-[(2-amino-1,6-dihydro-6-oxo-9H-purin-9-yl)methyl]phenyl]ethynyl]phosphonic acid, and
[2-[2-[(2-amino-1,6-dihydro-6-oxo-9H-purin-9-yl)methyl]phenyl]ethenyl]phosphonic acid.

3. A method of inhibiting purine nucleoside phosphorylase in a patient in need thereof which comprises administering to the patient an effective amount of a compound of the formula

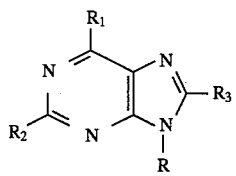 (I)

the tautomeric forms thereof, and the pharmaceutically acceptable salts thereof, wherein R is

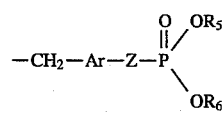

with Ar being a R$_9$-substituted phenyl, to which its adjacent CH$_2$ moiety is bonded to one ring carbon atom and the Z moiety is bonded to a second ring carbon atom of the Ar moiety, Z is a moiety selected from the group consisting of sub-types (a), (b), (c), (d), or (e) wherein (a) is

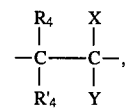

(b) is

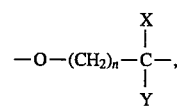

(c) is

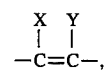

(d) is —C≡C—, and
(e) is

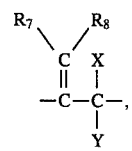

wherein n is an integer of 1 to 5 or zero;
R$_1$ is —OH or —SH;
R$_2$ is H or —NH$_2$;
R$_3$ is H, —NH$_2$, —OH, or —NH—NH$_2$;
R$_4$ is H;
R'$_4$ is H, OH or F, or R$_4$ and R'$_4$, together with the carbon atom to which they are attached, form a keto moiety;
R$_5$ is C$_{1-6}$ alkyl or H;
R$_6$ is C$_{1-6}$ alkyl or H;
R$_7$ is H, F, or C$_{1-4}$ alkyl;
R$_8$ is H, F, or C$_{1-4}$ alkyl;
R$_9$ is H, Cl, Br, C$_{1-6}$ alkyl, C$_{1-6}$ alkoxy, OH, NH$_2$ or CH$_3$;
X and Y are H, F or Cl, with the proviso that when n is zero, X and Y are both H.

4. A method according to claim 3 wherein said compound is selected from the group consisting of
[2-[2-[(2-amino-1,6-dihydro-6-oxo-9H-purin-9-yl)methyl]phenyl]-1,1-difluoroethyl]phosphonic acid,
[2-[2-[(2-amino-1,6-dihydro-6-oxo-9H-purin-9-yl)methyl]phenyl]-1-fluoroethenyl]phosphonic acid,
[2-[2-[(2-amino-1,6-dihydro-6-oxo-9H-purin-9-yl)methyl]phenyl]-1,1,2-trifluoroethyl]phosphonic acid,
[2-[2-[(2-amino-1,6-dihydro-6-oxo-9H-purin-9-yl)methyl]phenyl]-2-hydroxy-1,1-difluoroethyl]phosphonic acid,
[2-[2-[(2-amino-1,6-dihydro-6-oxo-9H-purin-9-yl)methyl]phenyl]-2,2-dihydroxy-1,1-difluoroethyl]phosphonic acid,
[3-[2-[(2-amino-1,6-dihydro-6-chloro-9H-purin-9-yl)methyl]phenoxy]-1,1-difluoropropyl]phosphonic acid,
[2-[(2-amino-1,6-dihydro-6-oxo-9H-purin-9-yl)methyl]phenoxy]methylphosphonic acid,

[2-[2-[(2-amino-1,6-dihydro-6-oxo-9H-purin-9-yl)methyl]phenyl]-1,1-difluoro-2-propenyl]phosphonic acid,
[2-[2-[(2-amino-1,6-dihydro-6-oxo-9H-purin-9-yl)methyl]phenyl]ethynyl]phosphonic acid, and
[2-[2-[(2-amino-1,6-dihydro-6-oxo-9H-purin-9-yl)methyl]phenyl ethenyl]phosphonic acid.

* * * * *